United States Patent [19]

Noishiki et al.

[11] Patent Number: 4,833,200

[45] Date of Patent: May 23, 1989

[54] ANTITHROMBOGENIC MEDICAL MATERIAL AND METHOD OF PREPARING SAME

[75] Inventors: Yasuharu Noishiki, Tottori; Teruo Miyata, Tokyo, both of Japan

[73] Assignee: Koken Co., Ltd., Tokyo, Japan

[21] Appl. No.: 889,654

[22] Filed: Jul. 25, 1986

[30] Foreign Application Priority Data

Jul. 31, 1985 [JP] Japan ................... 60-168857

[51] Int. Cl.$^4$ ............................ A61L 17/00
[52] U.S. Cl. ........................ 525/54.2; 514/2;
  514/56; 514/801; 514/822; 523/112
[58] Field of Search ........ 514/2, 56, 801, 822;
  530/356; 523/112; 525/54.2

[56] References Cited

U.S. PATENT DOCUMENTS

| | | | |
|---|---|---|---|
| 4,175,182 | 11/1979 | Schmer | 536/21 |
| 4,690,973 | 9/1987 | Noishiki et al. | 525/54.1 |
| 4,704,131 | 11/1987 | Noishiki et al. | 424/95 |

FOREIGN PATENT DOCUMENTS 0092414 10/1983 European Pat. Off. .
58-180162 11/1983 Japan .
60-203264 7/1985 Japan .

OTHER PUBLICATIONS

Noishiki et al., "A Simple Method to Heparinize Biological Materials", *J. of Biomed. Mat. Res.*, vol. 20, 337–346, (1986).

*Primary Examiner*—John Kight
*Assistant Examiner*—Nathan M. Nutter
*Attorney, Agent, or Firm*—Armstrong, Nikaido, Marmelstein, Kubovcik & Murray

[57] ABSTRACT

An antithrombogenic medical material with a remarkable antithrombogenic property and histocompatibility as well as sufficient physical strength, formed by fixing a heparinized collagen to a synthetic polymer material is provided. And a method of preparing an antithrombogenic medical material is provided, wherein a synthetic polymer material is subjected to a coating or impregnating treatment with a collagen-containing solution, followed by heparinization of the collagen, and the heparinized collagen is fixed to the synthetic polymer material. This method allows manufacturing of antithrombogenic medical material with ease.

7 Claims, No Drawings

ANTITHROMBOGENIC MEDICAL MATERIAL AND METHOD OF PREPARING SAME

BACKGROUND OF THE INVENTION

1. Field of the Invention

The present invention relates to an antithrombogenic medical material and a method of preparing same.

2. Description of the Prior Art

Many medical materials used in the treatment of cardiovascular diseases are required to possess antithrombogenic properties. For instance, in the case of artificial blood-vessels, artificial valves, artificial hearts, and parts of artificial lung devices, if the surfaces coming into contact with blood possessing blood coagulating properties, serious problems such as thrombosis may arise. In order to alleviate such problems, a veriety of antithrombogenic medical materials consisting of synthetic polymer materials have been developed so far. These materials, however, do not always possess sufficient compatibility with endothelial cells and other cells in the living tissues, and therefore with these materials it was difficult to obtain satisfactory antithrombogenic properties. Japanese Patent Laid-Open No.58-180162 proposes medical materials that are produced by imparting antithrombogenic properties to the natural tissues consisting predominantly of collagen of animal origin. There are various problems with natural tissues, however, that they differ to a great extent among individuals, that they have less physical strength and less homogeneity than synthetic polymer materials, that they are expensive, and that they are hardly available in large quantities.

OBJECT AND SUMMARY OF THE INVENTION

It is therefore an object of the present invention to provide an antithrombogenic medical material that maintains antithrombogenic properties for a long period of time, possesses high physical strength and superior homogeneity based on synthetic polymer materials, and can be produced at low cost and in large quantities.

It is also an object of the present invention to provide a method of preparing an antithrombogenic medical material that maintains antithrombogenic properties for a long period of time, possesses high physical strength and superior homogeneity based on synthetic polymer materials, and can be produced at low cost and in large quantities.

An antithrombogenic medical material according to the present invention is a composite formed by fixing a synthetic polymer material to a heparinized collagen, in which heparin is attached to a protamine which is fixed to a collagen through a cross-linking agent.

A method of preparing an antithrombogenic medical material according to the present invention comprises the steps of subjecting a synthetic polymer material to a coating or impregnating treatment with a collagen-containing solution and heaarinizing the collagen by fixing a protamine to the collagen through a cross-linking agent and by fixing heparin to the protamine.

DETAILED DESCRIPTION OF THE INVENTION

The synthetic polymer material used in the present invention may be, for example, a polyurethane, polyvinyl chloride, polyvinyl chloride copolymer, polyester, fluororesin, polycarbonate, polystyrene, and polyethylene. Shapes of these synthetic polymer materials may be convenientl chosen according to the application, and they may be, for example, in the form of membranes, knitted or woven tubes, or porous tubes, or parts in artificial lung devices.

The collagen used in the present invention may be one collected and purified from any tissue and may be atelocollagen which is prepared by removing telopeptides from a denatured collagen by a pepsin treatment, or may be its derivatives. In addition, the term "collagen" referred to in the present invention includes gelatin. Gelatin, being a protein derived from collagen, is obtained by thermal denaturation of collagen. That is, gelatin is obtained by treating a collagen at a temperature higher than its denaturation temperature (higher than about 37° C.) to destroy the helix structure of the collagen, and is also called denatured collagen. The gelatin used in the present invention can be commercially available one (for example, one available from Wako Junyaku K.K.), however, it is preferable to use gelatin which is obtained by treating atelocollagen at 50° C. for 2 hours. Glycerol can be used as a plasticizer for collagen.

The protamine used in the present invention, which is a basic nucleoprotein, can be any one collected and purified from any animal, and may contain histone. However, the protamine in the form of salt-like combination with an inorganic acid or an organic acid is preferred, and in particular, protamine sulfate or protamine hydrochloride is preferred.

The cross-linking agent used in the present invention may be, for example, bifunctional cross-linking agent such as hexamethylene diisocyanate, tolylene diisocyanate, and glutaraldehyde.

The heparinized collagen in the present invention is formed by covalent bonding of $\epsilon$-$NH_2$ groups of collagen side chains with $\alpha$-$NH_2$ groups of protamine through bifunctional cross-linking agent, and by ionic bonding of protamine which is a strong basic protein, with heparin which is an acidic mucopolysaccharide.

In the present invention, it is preferred that a synthetic polymer material is subjected to a coating or impregnating treatment with a solution containing collagen and protamine, and after drying, the material is immersed in a solution containing a cross-linking agent to fix the protamine to the collagen, and is further immersed in a heparin solution to attach heparin to the protamine.

It is also preferred in the present invention that a synthetic polymer material is subjected to a coating or impregnating treatment with a solution containing collagen, protamine, and heparin, and after drying, the material is immersed in a solution containing a cross-linking agent to fix the protamine to the collagen so as to obtain a heparinized collagen.

The present invention will be understood more readily by reference to the following examples; however, the examples are intended to merely illustrate the present invention and are not to be construed whatsoever to limit the scope of the present invention.

DETAILED DESCRIPTION OF THE PREFERRED EMBODIMENTS

EXAMPLE 1

A polyester tube (inner diameter: 6 mm) for an artificial blood-vessel, prepared by knitting polyester fibers, was employed as a synthetic polymer material.

A 1% aqueous solution (pH 3) of atelocollagen extracted from bovine dermis by using pepsin was prepared and poured into the hollow of the above-described tube, one end of which was closed. The tube wall was sufficiently impregnated with the solution by applying air pressure of 100 mmHg for one hour, and the excess of the atelocollagen solution was removed. The tube was subsequently immersed in a 1% glycerol aqueous solution for 10 seconds followed by immersion in a 1% ammonia water for 20 seconds, and then, air-dried. The operation cycle from the pouring of the atelocollagen aqueous solution to the air-drying was repeated ten times to yield a composite in which the atelocollagen was fixed to the polyester tube. With one end of the tube closed, the hollow of the composite was filled with protamine sulfate aqueous solution (concentration: 10%), and after one hour, the excess of the solution was removed. The tube hollow was then filled with a 1% glutaraldehyde aqueous solution (pH 7), and the tube was allowed to stand for 24 hours at room temperature so as to fix the protamine to the atelocollagen through the glutaraldehyde. The composite was then washed well with water and was immersed in a 1% heparin aqueous solution at room temperature for one hour, and was subsequently washed well with water and immersed in a 1% glycerol aqueous solution followed by air-drying, thus providing an artificial blood-vessel having smooth inner and outer surfaces

EXAMPLE 2

A mixed solution was prepared by mixing 50 ml of a 2% atelocollagen aqueous solution (pH 3) with 50 ml of a 10% protamine sulfate aqueous solution and stirring it well. One end of a tube for an artificial blood-vessel (inner diameter: 6 mm) prepared by knitting polyester fibers was closed, and the hollow of the tube was filled with the mixed solution. The tube wall was impregnated with the mixed solution by applying air pressure of 100 mmHg for one hour, and the excess of the solution was then removed. After freeze-drying, the tube so treated was immersed in a 5% hexamethylene diisocyanate solution for one hour to fix the protamine to the collagen through the hexamethylene diisocyanate. Subsequently, the tube was washed well with methanol, and was then immersed in a 1% heparin aqueous solution at room temperature for one hour, washed well with water, and freeze-dried again to yield an artificial blood-vessel.

EXAMPLE 3

An impregnating solution was prepared by mixing 30 ml of a 3% atelocollagen aqueous solution (pH 3) with 30 ml of a 10% protamine hydrochloride aqueous solution (pH 3) and 30 ml of a 1% heparin aqueous solution. The resulting mixed solution was added with 0.1 g of glycerol, and was then neutralized with 1N NaOH to pH 7.4.

One end of a tube for an artificial blood-vessel (inner diameter: 6 mm) formed of porous polytetrafluoroethylene was closed, and the hollow of the tube was filled with the impregnating solution. The tube wall was impregnated with the impregnating solution by applying air pressure of 100 mmHg for one hour, and the excess of the impregnating solution was then removed. The tube, after freeze-drying, was immersed in a 5% hexamethylene diisocyanate solution for one hour to fix the protamine to the collagen through the hexamethylene diisocyanate. The tube was then washed well with methanol and air-dried to yield an artificial blood-vessel.

EXAMPLE 4

An aqueous dispersion was prepared by adding 1 g of protamine sulfate, 100 ml of water and 0.8 ml of 1N NaOH to 1 g of a tendon collagen, an insoluble powdered collagen purified from bovine Achilles tendon, and by stirring the resulting mixture well with a homogenizer.

One end of a tube for an artificial blood-vessel (inner diameter: 6 mm) prepared by knitting polyester fibers was closed, and the hollow of the tube was filled with the dispersion. The collagen was forced into holes in the tube wall by applying air pressure of 200 mmHg, and a 1% ammonia aqueous solution was infiltrated from outside the tube for neutralization. After one hour, the excess of the dispersion was removed from the tube hollow and the tube was then freeze-dried. The tube was subsequently immersed in a methanol solution containing 2% hexamethylene diisocyanate, thereby fixing the protamine to the collagen, and the tube was then immersed in a 1% heparin aqueous solution for one hour at room temperature to effect heparinization. The resulting tube was washed with water and again freeze-dried to yield an artificial blood-vessel.

EXAMPLE 5

When each of the artificial blood-vessels obtained in Examples 1 to 4 was implanted in the descending thoracic aorta of a dog, each vessel exhibited remarkable antithrombogenic properties and histocompatibility without causing any thrombosis over a long period of time, together with favorable growth of endothelial cells.

EXAMPLE 6

90 g of water was added to 10 g of gelatin (dry) and the resulting mixture was heated to 90° C. to dissolve gelatin thoroughly. After the resulting solution was cooled to 50° C., 1 g of protamine sulfate and 0.1 g of heparin were dissolved in the solution. A coating solution containing gelatin, protamine and heparin was thus prepared.

The inner surface of a polycarbonate box portion connected to the hollow fiber in the circuit of an artificial lung device was subjected to surface treatment by radio frequency discharge using a plasma discharge device (Tesla Coil K type pinhole tester manufactured by Tokyo Koshuha Denkiro K.K.) for one hour to make the surface hydrophilic. Immediately after the surface treatment, the coating solution was poured into the box portion, and the surplus of the coating solution was removed therefrom after the inner surface was well wetted. The box portion was subsequently cooled to 5° C. to form a gel of the coating solution on the inner surface, and then immersed in a 1% glutaraldehyde aqueous solution (pH 8) for one hour at room temperature, and the box portion was washed well with water, and was then immersed in a 5% glycerol aqueous solution for one hour followed by air-drying.

In the circuit of the artificial lung device, thrombi are likely to be formed because blood may pool in the box portion. It was noted, however, that the box portion with heparinized gelatin coated on its inner surface obtained in this example did not form any thrombus over a long period of time.

We claim:

1. A method of preparing an antithrombogenic medical material consisting essentially of impregnating or coating a synthetic polymer material with a collagen by contacting the synthetic polymer material with a solution or a dispersion containing the collggen, drying the collagen impregnated or coated synthetic polymer material, treating the dried collagen impregnated or coated synthetic polymer material with a protamine and a cross-linking agent to cross-link the protamine to the collagen, and treating the cross-linked collagen and protamine impregnated or coated synthetic polymer material with a solution containing heparin, whereby the heparin is ionically bound to the protamine.

2. A method of preparing an antithrombogenic medical material, consisting essentially of impregnating or coating a synthetic polymer material with a collagen and a protamine by contacting the synthetic polymer material with a solution or a dispersion containing the collagen and the protamine, drying the collagen and protamine impregnated or coated synthetic polymer material, treating the dried collagen and protamine impregnated or coated synthetic polymer material with a cross-linking agent to cross-link the protamine to the collagen, and treating the cross-linked collagen and protamine impregnated or coated synthetic polymer material with a solution containing heparin, whereby the heparin is ionically bound to the protamine.

3. A method of preparing an antithrombogenic medical material, consisting essentially of impregnating or coating a synthetic polymer material with a collagen, a protamine and heparin by coating the synthetic polymer material with a solution or a dispersion containing the collagen, the protamine and heparin, drying the collagen, protamine and heparin impregnated or coated synthetic polymer material, and treating the dried collagen, protamine and heparin impregnated or coated synthetic polymer material, wherein the heparin is ionically bound to the protamine, with a cross-linking agent to cross-link the protamine to the collagen.

4. A method according to any one of claims 1, 2 or 3, wherein the synthetic polymer material is at least one member selected from the group consisting of a polyurethane, polyvinyl chloride, polyvinyl chloride copolymer, polyester, fluororesin, polycarbonate, polystyrene, and polyethylene.

5. A method according to any one of claims 1, 2 or 3, wherein the synthetic polymer material is at least one member selected from the group consisting of a membrane, or a woven, knitted, or porous tube.

6. A method according to any one of claims 1, 2 or 3, wherein the cross-linking agent is at least one member selected from the group consisting of hexamethylene diisocyanate, tolylene diisocyanate, and glutaraldehyde.

7. A method according to any one of claims 1, 2 or 3, wherein the protamine is at least one member selected from the group consisting of protamine sulfate and protamine hydrochloride.

* * * * *